(12) United States Patent
De Ziegler

(10) Patent No.: US 7,727,155 B2
(45) Date of Patent: Jun. 1, 2010

(54) MEDIUM FOR CONTRAST ENHANCEMENT OR CONVENIENCE FOR ULTRASONIC, ENDOSCOPIC, AND OTHER MEDICAL EXAMINATIONS

(75) Inventor: Dominique De Ziegler, Bellevue (CH)

(73) Assignee: Ultrast LLC, Oceanside, NY (US)

( * ) Notice: Subject to any disclaimer, the term of this patent is extended or adjusted under 35 U.S.C. 154(b) by 418 days.

(21) Appl. No.: 10/982,879

(22) Filed: Nov. 8, 2004

(65) Prior Publication Data

US 2005/0171419 A1    Aug. 4, 2005

Related U.S. Application Data

(63) Continuation of application No. PCT/EP03/04834, filed on May 8, 2003.

(60) Provisional application No. 60/378,640, filed on May 9, 2002, provisional application No. 60/428,145, filed on Nov. 18, 2002.

(51) Int. Cl.
*A61B 8/14* (2006.01)
(52) U.S. Cl. .................................................. 600/458
(58) Field of Classification Search ................. 600/438, 600/441, 456, 458; 128/662.02, 660.07, 128/660.01, 9.51, 9.5, 9.52, 450; 424/4; 252/312, 351
See application file for complete search history.

(56) References Cited

U.S. PATENT DOCUMENTS

| | | | | |
|---|---|---|---|---|
| 5,107,842 | A | * | 4/1992 | Levene et al. ................. 424/9.5 |
| 5,373,846 | A | * | 12/1994 | Widder ........................ 600/458 |
| 5,385,147 | A | | 1/1995 | Anderson et al. ......... 128/662.02 |
| 5,879,713 | A | * | 3/1999 | Roth et al. .................... 424/489 |
| 6,033,645 | A | * | 3/2000 | Unger et al. ................. 424/9.5 |

FOREIGN PATENT DOCUMENTS

DE    858 457 C    12/1952

(Continued)

OTHER PUBLICATIONS

Davies, A.C. et al., "The Use of a Low-Osmolality Contrast Medium in Hysterosalpingography: Comparison with a Conventional Contrast Medium," *Clin. Radiol.*, vol. 36, No. 5, pp. 533-536 (1985).

(Continued)

*Primary Examiner*—Brian Casler
*Assistant Examiner*—Elmer Chao
(74) *Attorney, Agent, or Firm*—Winston & Strawn LLP

(57) ABSTRACT

The present invention relates to a particularly convenient medium for providing contrast enhancement and/or distension of the subject body or organ cavity during imaging, radiographic, visualization, or other similar medical examinations, including ultrasound, endoscopic examinations, MRI, x-ray, hystero-salpingograms, CT scans, and similar procedures. The present invention provides the contrast enhancement and/or distends the body or organ cavity without constant leakage of the medium or the resulting need to constantly or repeatedly infuse additional medium. The medium is designed to have sufficient viscosity or consistence initially to remain in the body or organ cavity for a time generally sufficient to complete the procedure, and then to facilitate easy removal or expulsion from the cavity, preferably by liquefying or losing viscosity. The phase or viscosity change may be triggered by a variety of factors that liquefy or otherwise facilitate easy removal or expulsion of the composition from the cavity.

21 Claims, 5 Drawing Sheets

FOREIGN PATENT DOCUMENTS

| | | |
|---|---|---|
| EP | 1 034 796 A | 9/2000 |
| JP | 61-149128 | 7/1986 |
| JP | 4-024024 | 1/1992 |
| JP | 11-235337 | 8/1999 |
| JP | 11-318898 | 11/1999 |
| JP | 2001-097847 | 4/2001 |
| NL | 9 400 762 A | 12/1995 |
| WO | WO 94/07417 | 4/1994 |
| WO | WO 95/08351 | 3/1995 |

OTHER PUBLICATIONS

Haage, P. et al,. "Gadolinium Containing Contrast Agents for Pulmonary Ventilation Magnetic Resonance Imaging Preliminary Results," *Invest. Radiol.*, vol. 37, No. 3, pp. 120-125 (2002).

Knopp, M.V. et al., "Effect of viscosity, cannula size and temperature in mechanical contrast medium application in computed tomography and magnetic resonance imaging," *Fortschr. Röntgenstr.*, vol. 163, No. 3, pp. 259-264 (1995). (Original in German with English translation).

Ophir, J. et al., "Contrast Agents in Diagnostic Ultrasound," *Ultrasound in Med. & Biol.*, vol. 15, No. 4, pp. 319-333 (1989).

Roncuzzi, R. et al., "Evaluation of the Diagnostic Possibilities of a Viscose Water-Soluble Contrast Medium for Hysterosalpingographic Examination in Female Sterility," *Attualita di Ostetrica e Ginecologia*, Societa Editrice Universo, Rome, Italy, vol. 14, No. 6, pp. 605-630 (1968).

Rubin, D. L. et al., "Influence of Viscosity on Win 39996 as a Contrast Agent for Gastrointestinal Magnetic Resonance Imaging," *Invest. Radiol.*, vol. 30, No. 4, pp. 226-231 (1995).

Shirk, G. et al., "The Use of Low-Viscosity Fluids for Hysteroscopy," *J. Am. Assoc. Gyn. Laparoscopists*, vol. 2, No. 1, pp. 11-21 (1994).

Warren, P.S. et al., "The Liquid-Filled Stomach—An Ultrasonic Window to the Upper Abdomen," *J. Clin. Ultrasound*, vol. 6, No. 5, pp. 315-320 (1978).

Ikeda, T. et al., "The Separation Procedure for Intrauterine Adhesion (Synechia Uteri) Under Roentgenographic View," *Fertility and Sterility*, vol. 36, No. 3, pp. 333-338, Sep. 1981.

\* cited by examiner

MEDIUM FOR CONTRAST ENHANCEMENT OR CONVENIENCE FOR ULTRASONIC, ENDOSCOPIC, AND OTHER MEDICAL EXAMINATIONS

CROSS-REFERENCE TO RELATED APPLICATIONS

This application is a continuation of co-pending International Application No. PCT/EP03/04834, filed on May 8, 2003, which claims the benefit of U.S. Provisional application No. 60/378,640, filed on May 9, 2002, and U.S. Provisional Application No. 60/428,145, filed on Nov. 18, 2002, the entire disclosures of which are hereby incorporated by reference herein.

FIELD OF INVENTION

The present invention relates to a particularly convenient medium for providing contrast enhancement or distension during imaging, radiographic, visualization, or other similar medical examinations and procedures involving a body or organ "virtual" cavity, including ultrasound, endoscopic examinations, MRI, x-ray, CT scans, and similar procedures jointly, "medical imaging procedures"). The present invention provides the contrast enhancement and/or distends a body or organ cavity that is normally virtual, without constant leakage of the medium or the need to constantly, repeatedly, or even frequently replace leaked contrast composition. The medium is designed to have sufficient consistency initially—whether as a solid, semi-solid, gel, or viscous fluid—to remain in the body or organ cavity for a time generally sufficient to complete the procedure, and then to liquefy or lose viscosity, facilitating easy removal or expulsion from the cavity. For imaging and radiographic examinations, the medium may provide enhanced contrast as well as the distension of the cavity. For visualization examinations, the medium typically would be optically transparent but provide the distension necessary for endoscopic vision.

The invention also relates to methods of conducting imaging, radiographic, visualization, or other similar medical examinations using the convenient medium.

BACKGROUND OF THE INVENTION

Ultrasonic and endoscopic examinations are frequently used for medical observation of various organs located in or near various body cavities. For example, the uterus is easily accessible to ultrasound imaging. New trans-vaginal probes, originally designed to facilitate egg retrieval in in vitro fertilization (IVF), have further enhanced the quality and usefulness of uterine ultrasound imaging. This improvement has directly resulted from the high frequency-high resolution ultrasound probes made possible by the proximity between the probe, inserted vaginally, and the organ being analyzed—in this case, the uterus.

Clinical circumstances warranting ultrasound imaging of the uterus fall into two main categories. During pregnancy, ultrasounds are very often used to assess fetal growth and well-being. And in non-pregnant women, ultrasounds frequently serve to identify uterine pathologies, such as fibroids or polyps, particularly while investigating the resulting symptoms such as bleeding disorders (dysfunctional uterine bleeding, or "DUB"), cramping, and infertility.

One striking difference between ultrasound imaging of the pregnant and non-pregnant uterus is the presence of amniotic fluid in the pregnant uterus. During pregnancy, the intrauterine (amniotic) fluid serves as a remarkable contrast enhancer that markedly improves the resolution of ultrasound images. The structures that are most affected by the contrast enhancement provided by the amniotic fluid are those lying in the immediate vicinity of fluid inter-phases, such as the central nervous system structures.

Learning from the unique advantages of ultrasound imaging during pregnancy and the role played by amniotic fluid as a contrast enhancer, several investigators have tried to reproduce these advantages for assessing the non-pregnant uterus. Thus, in order to similarly improve the quality of ultrasound imaging of a non-pregnant uterus, researchers have infused sono-transparent or sono-opaque fluids into the uterine cavity for providing, respectively, negative (black) or positive (white) contrast enhancement for the resulting images.

Most commonly, about 10-40 milliliters of 0.9% sodium chloride (NaCl, or saline) solution—a sono-transparent solution providing negative contrast—is slowly, and continually or repeatedly, infused into the uterine cavity in order to maintain appropriate pressure to distend the uterus during the ultrasound examination. This is usually done with plastic catheters designed for embryo transfers, or various other catheter models. The fluid must be continually or repeatedly infused because—as would happen with any pressurized fluid in an open container—it continually leaks out, in this instance through the cervix and/or fallopian tubes. Sometimes, a catheter may be equipped with an inflatable balloon or other sealing mechanism, which is intended to reduce leakage at the cervical end, but not at the tubes.

Today, such a procedure involving infusion of fluid during a uterine ultrasound procedure is most commonly referred to as a "sonohysterography," though it is also known by other names, including hysterosalpingo-contrast sonography (HyCoSY), saline hysterosonography, etc.

While simple in principle, the use of an intrauterine infusion of a NaCl or other solution as an ultrasound contrast enhancer is complex and cumbersome in practice. The intrauterine catheter connected to the NaCl syringe must be first introduced through the cervical canal into the uterus after a speculum is put in place. Then, the speculum needs to be removed while the catheter is held in the uterus, in order to accommodate the intra-vaginal ultrasound probe. Finally, the probe is inserted into the vagina with one hand, taking care not to displace the catheter, while the other hand holds the catheter and the syringe, pushing the plunger to initiate the intrauterine flow of fluid. Thus, a "3rd hand" is needed to make any necessary adjustments to the ultrasound machine, and to save iconographic documents.

The need to constantly flush contrast fluid through the uterine cavity while conducting the ultrasound examination, as it continually leaks out, also results in inconvenient and messy fluid puddles in the examination area, including on the examination table—which can be a further source of discomfort for the patient. Needless to say, sonohysterography is considered a time-consuming procedure by most gynecologists, who tend to use it reluctantly and only in certain cases that are deemed to warrant the extra inconvenience and discomfort. Despite these practical difficulties, the quality enhancement of ultrasound images achieved through sonohysterography is significant and allows more precise diagnoses of uterine pathologies, such as uterine fibroids and polyps, otherwise impossible or difficult to examine with plain ultrasounds.

Enhanced contrast ultrasounds provide better images of intrauterine pathologies. See, for example, FIGS. 1 through 4. FIGS. 1A, 2A, 3A, and 4A show the results of a plain uterine ultrasound in each of four patients. FIGS. 1B, 2B, 3B, and 4B show the results, respectively in the same four patients, of an enhanced contrast ultrasound using the medium of the instant invention. The substantially increased contrast and visibility attained with the instant invention is similar to that achieved even with typical sonohysterography (which would not provide the convenience and benefits of the instant invention, discussed below).

Numerous studies have validated the improvement provided by the addition of an intrauterine contrast medium over plain uterine sonography. Specifically, a wealth of data has demonstrated the superior positive and negative prediction value of saline sonohysterography for identifying intrauterine pathologies, when compared to the results and abilities of plain uterine ultrasounds. The pathologies easily identified by sonohysterography include submucosal fibroids and endometrial polyps, two common causes of dysfunctional uterine bleeding. Yet despite ample clinical value documented by many academic studies, actual use of sonohysterography remains relatively limited because of the difficulties and time-consuming nature of the procedure. It is for these practical reasons that sonohysterography is not commonly used in everyday gynecology.

One variation of saline sonohysterography uses sono-opaque solutions such as Echovist®-200, Albunex®, or similar products instead of the sono-transparent solutions such as normal saline, in order to render the uterine cavity hyperechogenic ("white") instead of hypoechogenic ("black"). The value of "white" hyperechogenic contrast over "black" hypoechogenic products such as saline has been debated.

For hysterosonography using hyperechogenic ("white") medium, the products used (Echovist and similar products) were designed for intra-vascular injection and contrast enhancement of cardiac ultrasounds. Hence, their use in obstetrics and gynecology has been an afterthought. They are all fluid and require infusion throughout the procedure, just like NaCl or other "black" hypoechogenic products. One claimed advantage of a hyperechogenic, or positive contrast, procedure is the resulting enhanced contrast image of the Fallopian tubes, particularly in their proximal segment, as compared to the relative lack of contrast when using negative contrast (such as saline) sonohysterography for such imaging.

Today, however, while many physicians recognize that positive contrast sonohysterography can be used to verify tubal patency, classic hysterosalpingography (HSG), an examination using x-rays, remains the primary mode for studying tubal anatomy because of the superior quality of tubal imaging obtained. While we agree that HSG is generally superior to positive contrast hysterosonography for assessing tubal anatomy, we believe that positive contrast hysterosonography may have a role to play for studying tubal functionality (peristaltic contractions).

Irrespective of its indications, positive contrast sonohysterography is as cumbersome a "3 hand" procedure as negative sonohysterography. It, too, requires simultaneously instilling the contrast fluid, holding the ultrasound probe, and making necessary adjustments on the ultrasound machine. As positive contrast preparations such as Echovist-200 are injectable, fluid preparations, the products typically still need to be continuously or periodically instilled during the examination. Hence, these procedures, too, require keeping the catheter in the uterine cavity during the procedure to allow continued or frequent replenishment of the medium, and commonly result in unpleasant watery leakages on the examination table.

Hysteroscopy, in contrast to ultrasound procedures, is an endoscopic investigation of the uterus intended to provide a direct visualization, rather than a contrast image. Accordingly, such a procedure typically does not require use of a contrast enhancing agent, but it still uses an "image enhancing" medium to distend the uterus, which otherwise is a virtual cavity—that is, one that is 'collapsed' and thus difficult to visualize. This type of procedure, however helpful, has significant disadvantages that prevent its widespread use. These disadvantages include pain and discomfort caused to the patient during the procedure, and the need to re-sterilize the expensive instruments after each examination.

During a hysteroscopy, the hysteroscope is introduced into the uterine cavity through the cervical os. In operative hysteroscopies, the procedure is conducted under anesthesia, which usually is general anesthesia, but may be a spinal or local (cervical block) anesthesia. The procedure typically requires dilatation of the cervix to approximately 7 to 9 mm to permit insertion of the relatively large instrument—the surgical hysteroscope. Constant infusion of a solution, such as a NaCl solution, Ringers, or glycine (if monopolar coagulation is envisioned), or of a gas, such as $CO_2$, is needed to constantly distend the cavity and to wash away bleeding.

In some circumstances, a thicker solution, such as Hyscon™ is infused during the hysteroscopy procedure. While sticky and slightly thicker than saline, Hyscon still does not distend the cavity by itself without being infused under pressure. And Hyscon, too, leaks out, so again the procedure requires constant or periodic infusion.

Hysteroscopes are typically configured in such a way that, if needed, mini-surgical instruments may be inserted through the hysteroscope to cut and remove abnormal structures such as polyps, sub-endometrial fibroids and scar tissue (synechiae), or to burn them away using electrocoagulation or laser beams. Accordingly, operative hysteroscopes tend to be anything but compact.

Office hysteroscopy is a simplified version, performed for diagnostic purposes only. The smaller instrument size used in office hysteroscopy (3-5 mm in diameter) allows the physician to avoid cervical dilatation and anesthesia. Nevertheless, pain and discomfort still accompany the procedure, and so resort to this form of the procedure, too, remains somewhat limited. As in operative hysteroscopy, a solution or a gas must be infused throughout the procedure, in order to distend the uterine cavity, thereby permitting visualization. Of course, the infusion itself (which takes place under pressure), and the typical accompanying mess of leaked fluid, are additional sources of discomfort for the patient.

Thus, a product that provides (1) the ultrasound contrast enhancing properties of negative or positive intrauterine contrast enhancers and slightly distends the uterine cavity for offering a contrast interphase but without the leakage requiring constant fluid perfusion during the ultrasound examination, or (2) the distension required for a hysteroscopy procedure while allowing optical clarity, but without the need for bulky apparatus to continually perfuse the medium, or both, would be a huge advance in both aspects of the field. Such a product would make the procedures less burdensome, uncomfortable, and messy, and more convenient and efficient.

Such a product should have gel-like viscosity, or otherwise be able to remain in the uterine cavity after intrauterine infusion for the duration of the examination. This would permit the physician to remove the speculum and intrauterine catheter after infusion, and to perform the ultrasound or hysteroscopy procedure freely without having to constantly infuse the product during the examination. One added advantage would be that images generated would be free of image artifacts generated by the intrauterine catheter. The ideal product should then liquefy after a reasonable period of time, or otherwise facilitate easy removal, so that it is not permanently retained, but rather expelled from the uterine cavity after completion of the ultrasound examination. Intrauterine retention of a substance remaining in viscous gel consistency would be improper because of the potential to interfere with fertility.

As used herein, an "image enhancing" medium means a medium that enhances or facilitates contrast and/or direct visualization during medical examination procedures, such as by distending a body or organ cavity during a procedure such as ultrasound or endoscopy, and/or by providing improved contrast during imaging procedures such as ultrasounds. Thus, contrast enhancement is used here more broadly than the pure sense of merely enhancing or improving a contrast image. Instead, we use the term herein, as appropriate in context, to refer to enhancing or facilitating imaging, radiographic, visualization and similar techniques generally, whether by literally increasing the contrast, or by facilitating distension of the surface being examined, or both.

As used herein, a "phase-changing" or "phase-shifting" medium is one that is more of a solid or semi-solid (such as a gel) initially in a body or organ cavity during a medical examination procedure, but then changes or shifts to more of a liquid to facilitate removal or expulsion from the cavity, preferably after the procedure is completed. In contrast, a "viscosity-changing" or "viscosity-shifting" medium is one that is more viscous when used in a body or organ cavity during a medical examination procedure, but then becomes less viscous to facilitate removal or expulsion from the cavity, preferably after the procedure is completed.

As used herein, a medium that is in a "solid," "semi-solid," or "gel" state or phase is in a form that is sufficiently stable physically (i.e., relatively solid or viscous rather than fluid or gaseous) to substantially remain in a body or organ cavity typically without requiring constant or frequent replenishment during a medical examination procedure.

As used herein, "sufficient time" to conduct a medical examination procedure is typically on the order of at least several minutes, generally about 3 to 10 minutes, and preferably about 5 to 7 minutes. By the time the inventive composition is in place for such a sufficient time, the procedure is generally completed. Whether or not it liquefies or decreases in viscosity, the composition then is allowed to leak from the body or organ cavity, or is removed quickly and easily. Generally the cavity is mostly free of the composition within about 7 to 20 minutes of its initial placement in the cavity, preferably within about 10 to 15 minutes.

As used herein, "medical imaging" refers to imaging, radiographic, visualization, or other similar procedures for examining body or organ cavities or contiguous tissue, for various purposes including evaluation, diagnosis, observation, treatment, etc., whether prompted by specific concerns or symptoms or simply as precautionary measures. Such procedures include, for example, ultrasound, endoscopic procedures, MRI, x-rays, hystero-salpingograms (HSG), and CT (Computed Tomography) scans (each a "medical imaging procedure"). Similarly, a medical imaging composition or medium is intended for use in such medical imaging procedures.

SUMMARY OF THE INVENTION

The invention relates to a medical imaging composition used for medical imaging procedures involving a body or organ cavity. The composition typically includes an image enhancing, viscosity-shifting medium having an initial viscosity or consistency that, upon or after introduction to a body or organ cavity, is sufficient to remain substantially in place within the cavity for a period of time sufficient for the imaging procedure to be completed. Advantageously, the composition also has a subsequent reduced viscosity or consistency that is sufficiently reduced so as to allow the medium to be easily expelled or removed from the body or organ cavity.

In one embodiment of the invention the medium is initially a solid, semi-solid, or gel upon or after introduction to a body or organ cavity so that the medium does not need to be continually or frequently administered during the imaging procedure. In this embodiment, the medium typically liquefies or decreases in viscosity after a period of time, so that it can be easily expelled or removed from the cavity.

In a particular embodiment of the invention, the medium is designed to have properties that render the composition suitable for use in vaginal ultrasound examinations.

In a further embodiment the medium is designed to liquefy or decrease in viscosity in response to a particular change in temperature of the composition.

The medium can include one or more polymers and optionally one or more adjuvants or treating agents. The adjuvants or treating agents used typically include an anti-infective agent or a radio opaque agent.

The invention also relates to a method of conducting a medical imaging procedure on a body or organ cavity. In one embodiment, the method comprises (a) placing the composition of the invention into a cavity, such as a uterus, (b) conducting the imaging procedure, and then (c) removing or allowing expulsion of the composition from the cavity.

The invention further relates to use of the medium of the invention in manufacturing an image enhancing composition for use in a medical imaging procedure involving a body or organ cavity. The medium used typically has sufficient viscosity so that it does not need to be continually or frequently administered during the procedure, and is easily expelled or removed from the cavity after sufficient time for the procedure normally to be completed.

In any of these embodiments, the initial viscous or solid, solid-like, or gel state may be partly or entirely provided by use of a polymer or other component of the medium.

The medium of the invention distends the body or organ cavity with less pressure, and allows medical imaging of the cavity without concomitant, constant infusion of additional medium. Good quality vision typically is possible until the medium liquefies, at which time the examination may deteriorate due to vision degradation or loss of the medium. The medium is intended to provide ample time for thoroughly exploring the uterine cavity without requiring any continual infusion, but if necessary to maintain the examination for a longer period of time, a second or further additional application generally can be employed.

BRIEF DESCRIPTION OF THE FIGURES

FIG. 1B reveals a positive finding for an endometrial polyp (10) that is not revealed in FIG. 1A. Histology confirmed the presence of a polyp.

FIG. 2B reveals a positive finding indicating a endometrial polyp or fibroid (11) that is not revealed in FIG. 2A. Histology confirmed the presence of a polyp.

Figure 1A:
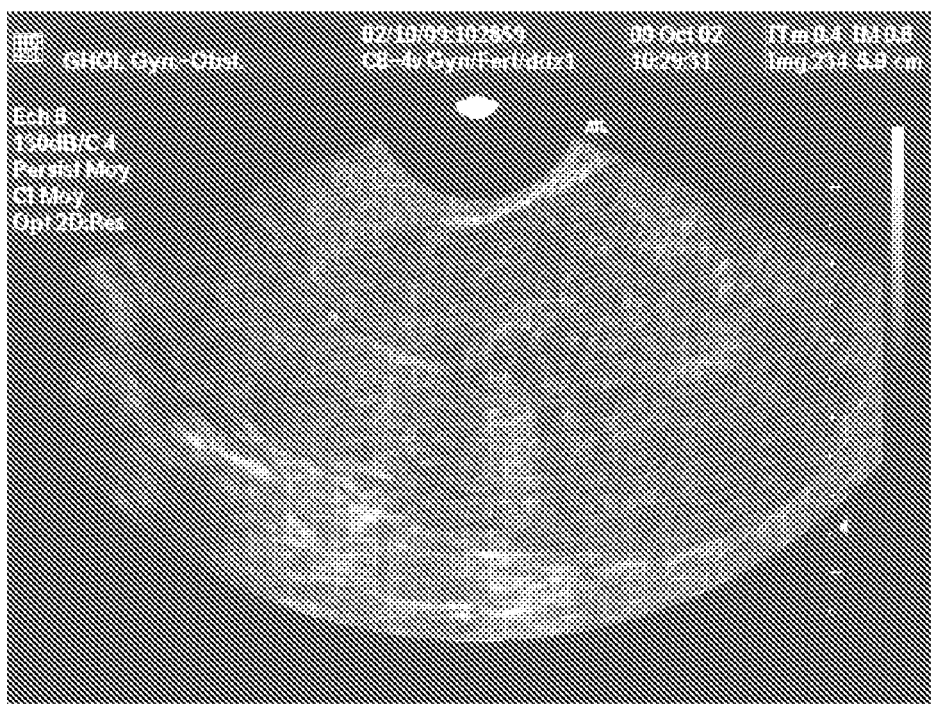
FIGS. 1A and 1B show, respectively, a plain ultrasound and an ultrasound using the instant invention, for patient #1.
Figure 1B:
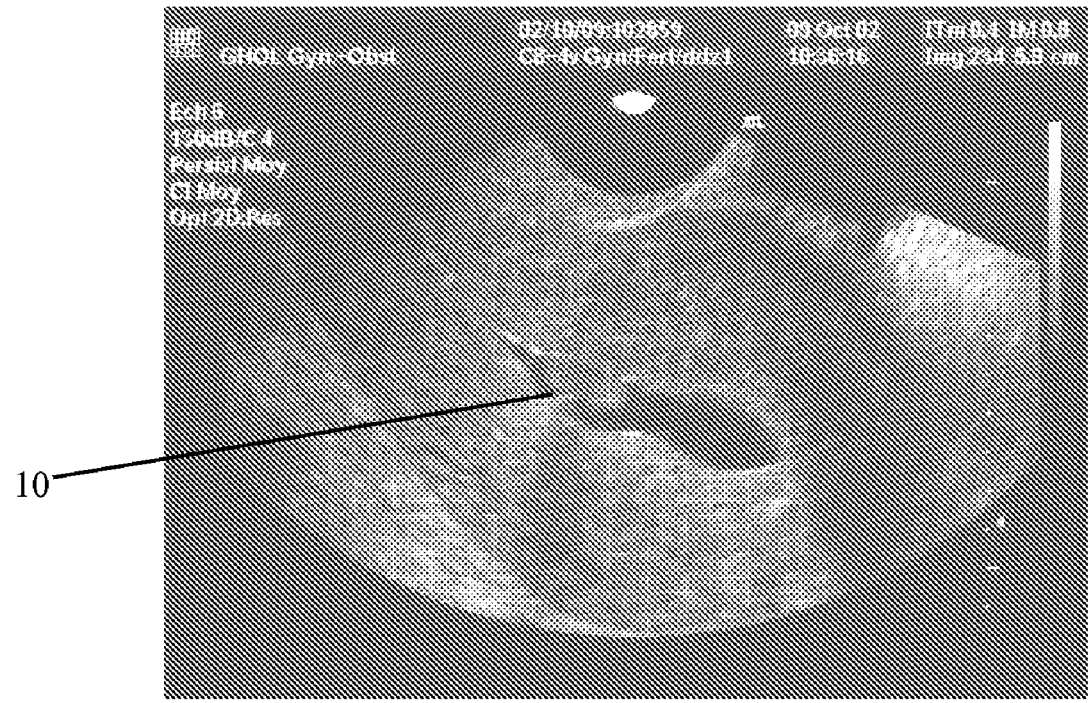
Figure 2A:
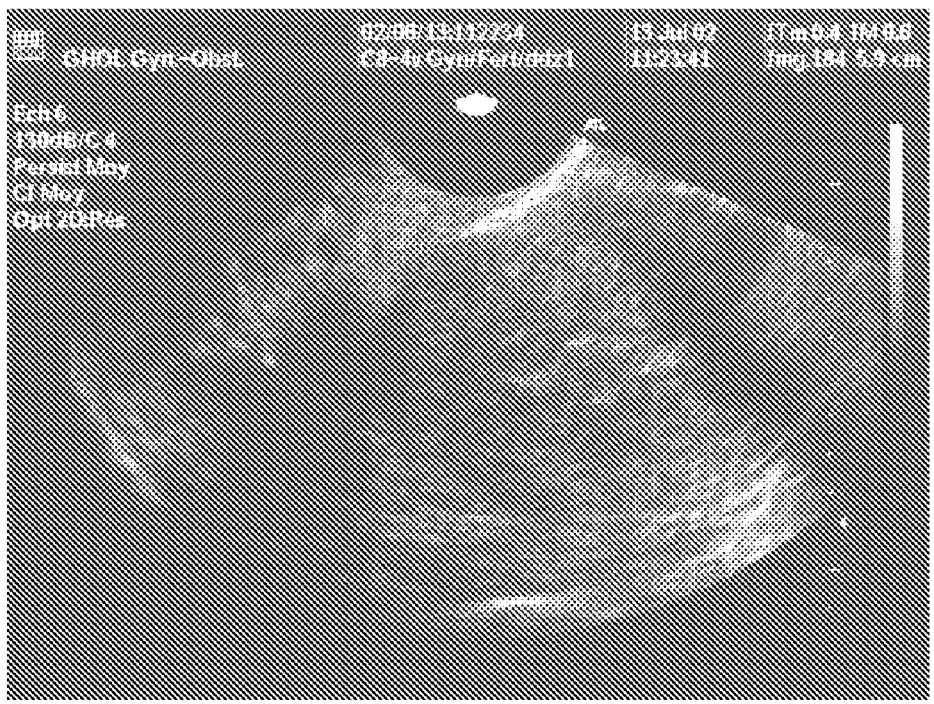
FIGS. 2A and 2B show, respectively, a plain ultrasound and an ultrasound using the instant invention, for patient #2.
Figure 2B:
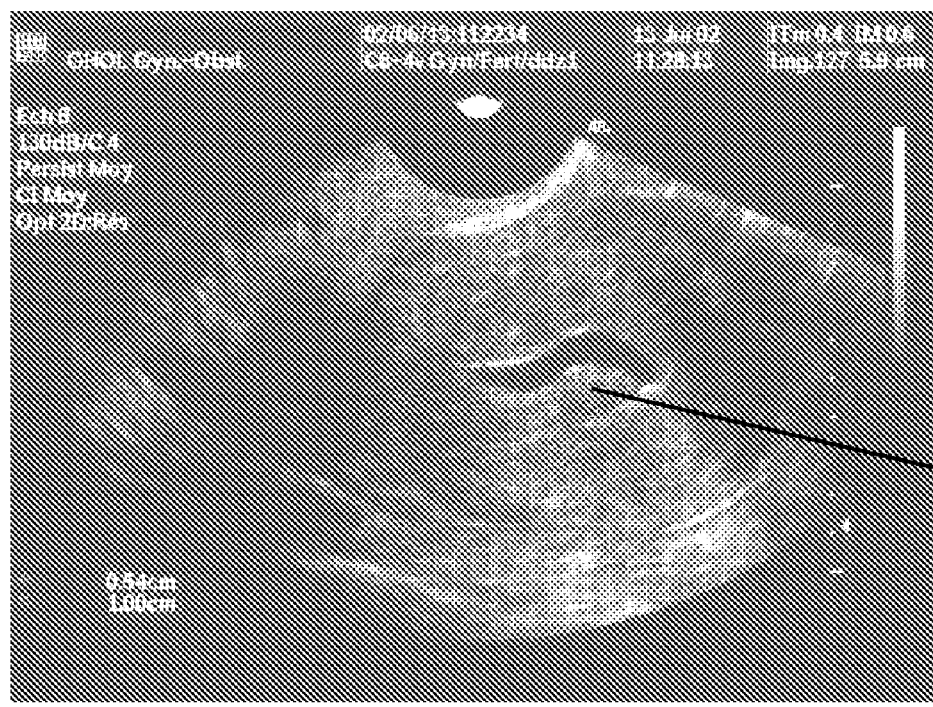
Figure 3A:
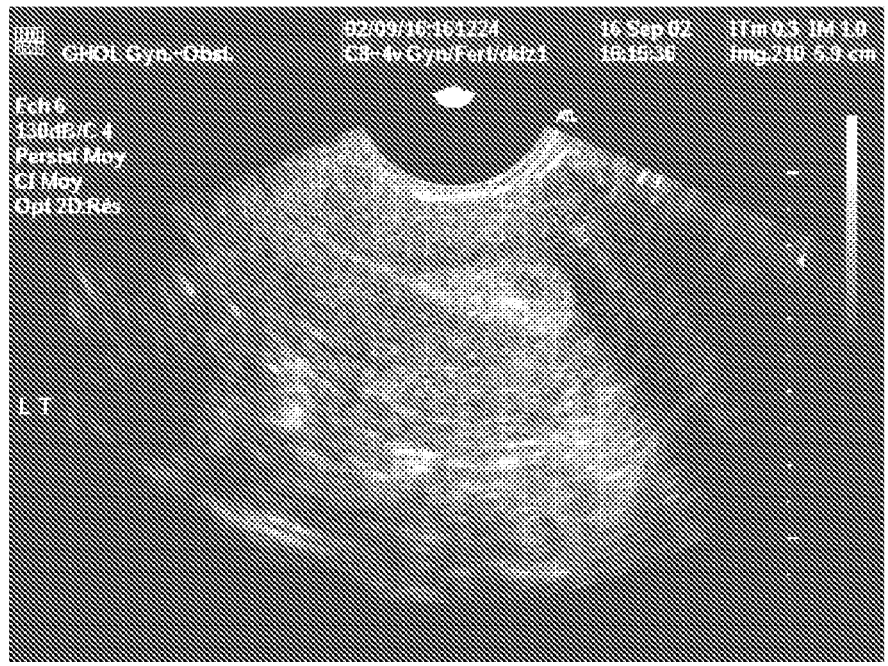
FIGS. 3A and 3B show, respectively, a plain ultrasound and an ultrasound using the instant invention, for patient #3. FIG.
Figure 3B:
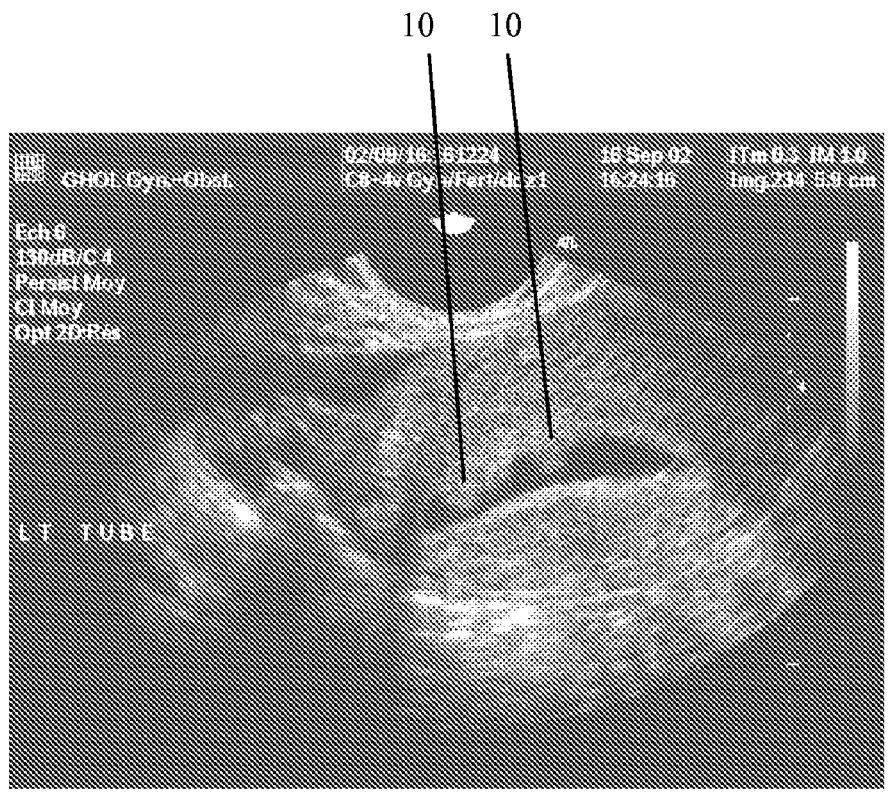

3B reveals a positive finding suggestive of an endometrial polyp (10) that is not revealed in FIG. 3A. Histology confirmed the presence of a polyp.

Figure 4A:
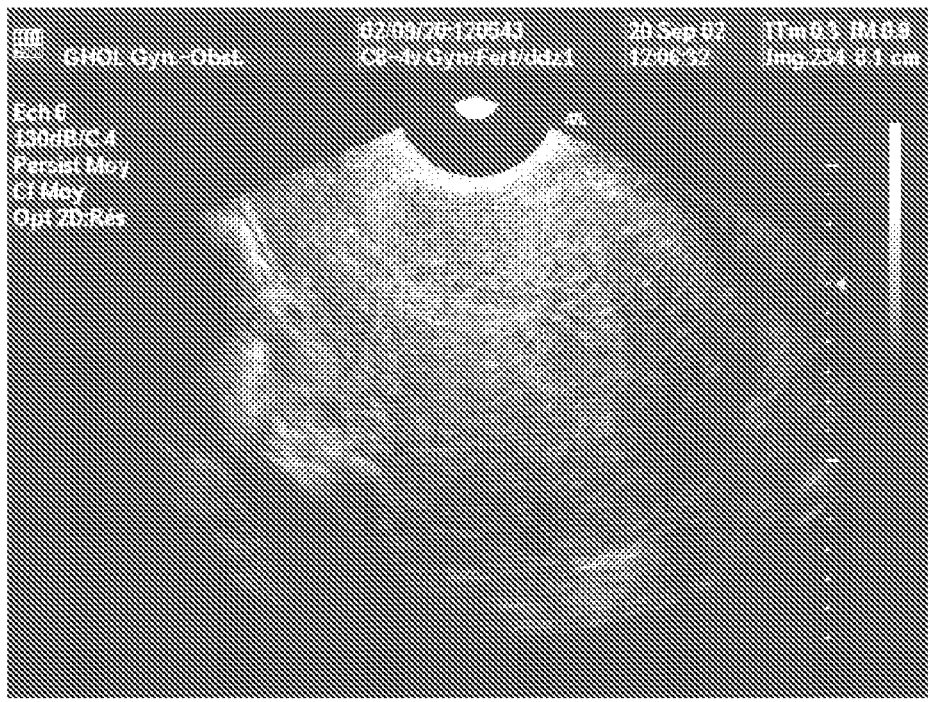
Figure 4B:
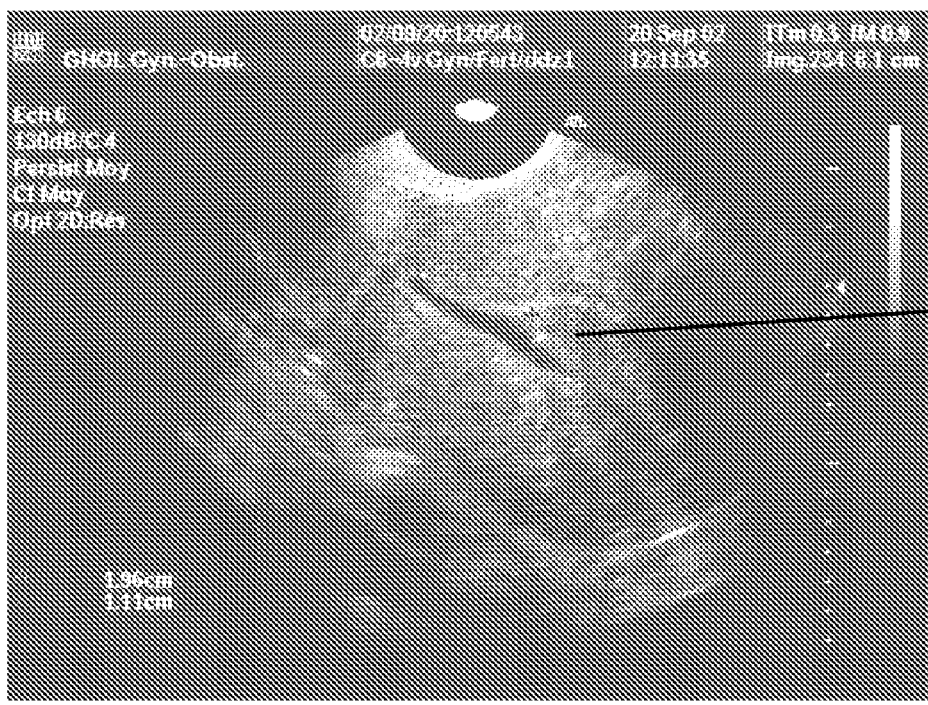

FIGS. 4A and 4B show, respectively, a plain ultrasound and an ultrasound using the instant invention, for patient #4. FIG. 4B reveals a positive finding suggestive of an endometrial polyp or fibroid (11) that is not revealed in FIG. 4A. Histology confirmed the presence of a fibroid.

Figure 5:
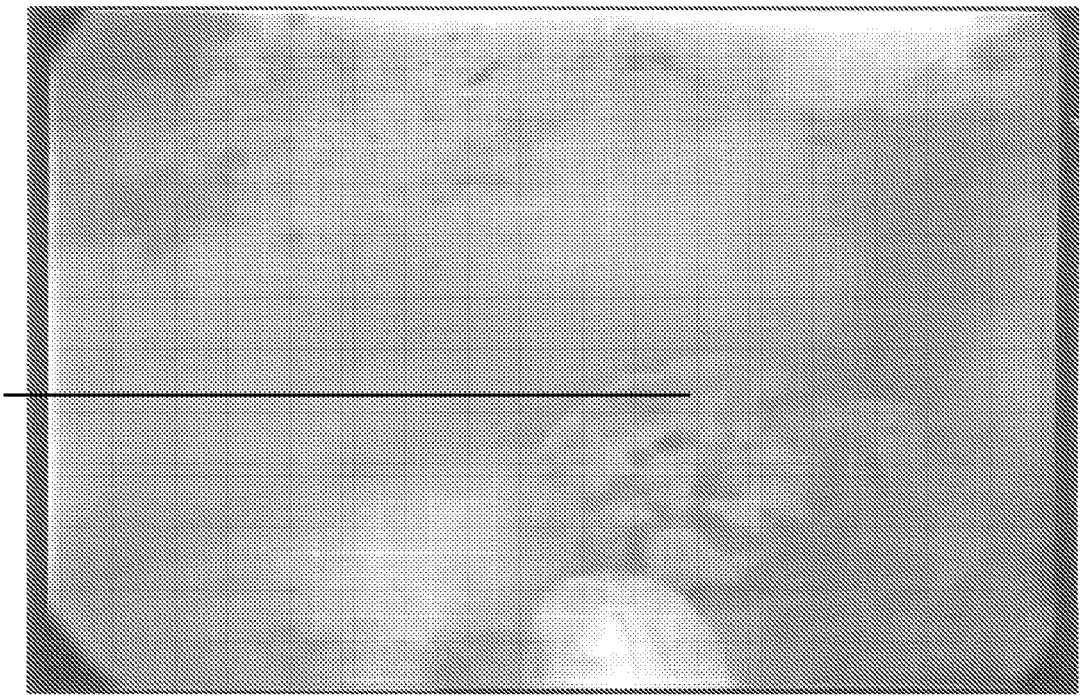
Figure 6:
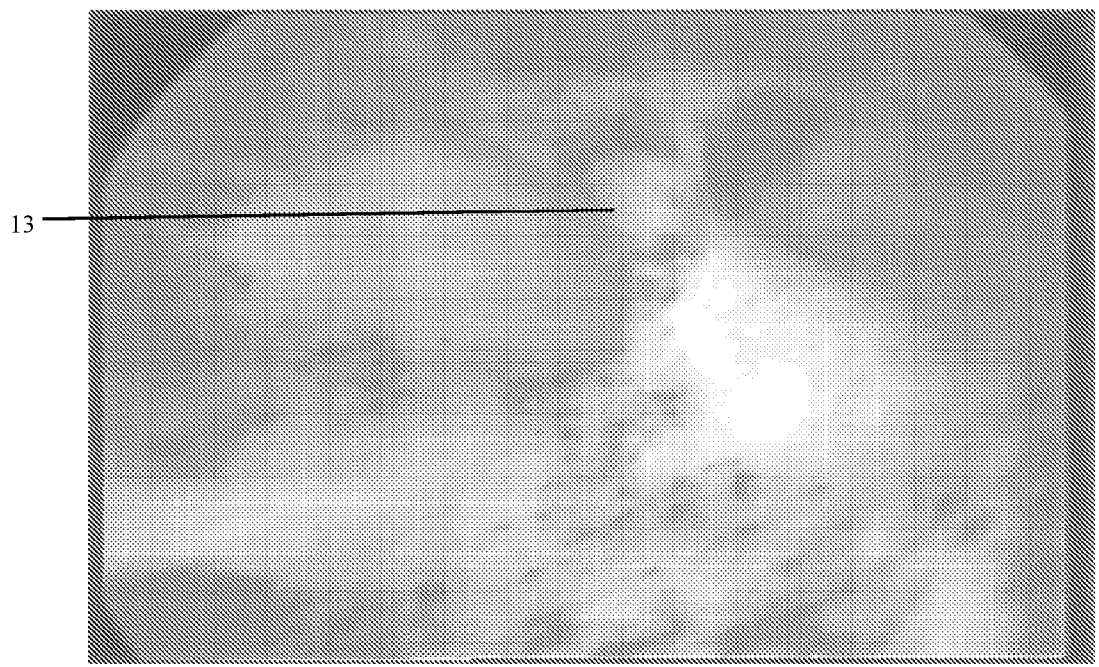

FIGS. 5 and 6 show hysteroscopy results of two other patients, using the instant invention. FIG. 5 shows a uterine polyp (12), while FIG. 6 shows a uterine synechia or scar (13). Both findings were confirmed by subsequent surgical hysteroscopy.

DETAILED DESCRIPTION OF THE INVENTION

The present invention provides convenient contrast enhancing compositions for use as media with medical imaging procedures (such as imaging, radiographic, visualization, or other similar medical procedures) for purposes such as examination, evaluation, diagnosis, treatment, observation, and check-ups, of body or organ cavities. The cavities typically are "virtual cavities," in that they tend to be collapsed and folded in, similar to an empty balloon, rather than expanded and open but empty.

Such procedures include, for example, ultrasound and endoscopic procedures, MRIs, x-rays, hystero-salpingograms, and CT scans. The medium would provide, as warranted and appropriate for the particular procedure, the contrast enhancing properties of a saline or similar infusion. The contrast enhancing effects can result from a "black" interphase such as provided by saline or a similar solution or from a "white" interphase provided by a hyperechogenic solution, such as Echovist. In both cases, the interphase provided by the contrast agent is different from the surrounding structures that appear in various shades of grey. Regardless of whether contrast enhancement is desired, the medium would also have the ability to remain in place without significant leakage or need for constant or periodic replenishment during the procedure, while changing phase or viscosity after a time sufficient to complete the procedure, or otherwise having the ability to be expelled or removed easily and readily from the body or organ cavity at that time.

The decreased pressure needed to instill such a medium decreases the patient's level of discomfort. The inventive medium typically could be infused at a lower pressure as it does not have to overcome the constant leakage through the cervix and tubes, and at pressure for much less time, than prior art media, while still adequately distending the body cavity or organ. This decrease in pressure and in duration of pressure would help minimize patient discomfort. Furthermore, the lack of abundant spillage through the tubes into the pelvic cavity during the procedure will further reduce the level of discomfort of the procedure using the invention.

The instant invention would be useful during various types of medical imaging procedures, whether for observational, diagnostic, treatment, or other purpose, including without limitation, classical "imaging" procedures such as x-rays, ultrasound, CT scans or MRI; radiographic studies such as HSG or CT scans; or direct visualization techniques such as endoscopy.

As discussed above, in ultrasounds performed on pregnant women, the amniotic fluid serves as an intrauterine contrast enhancer, providing a negative or "black" sonic interface. In the non-pregnant uterus, the uterine cavity is not as easily visualized due to the lack of a contrasting interface—the collapsed folds of the uterus, and the small pockets of air, do not present a detailed image. Hence, normal and pathological images (such as polyps, or sub-mucosal fibroids) are often insufficiently sharp to permit a definitive diagnosis.

Hysterosonography mimics the conditions of ultrasounds on pregnant women, and provides images of excellent quality. However, hysterosonography is cumbersome, time consuming, and awkward, and typically requires more than one person to perform. The instant invention seeks to provide the key benefits of hysterosonography while avoiding these major problems.

Hysterosonography using hyperechogenic ("white") medium has been advocated for studying uterine pathologies and tubal anatomy (patency). The products used (Echovist, and similar products) were designed for intra-vascular injection and contrast enhancement of cardiac ultrasounds. Its use in obstetrics and gynecology has been an afterthought. These products are fluid, and need to be infused throughout the procedure, just like a NaCl solution.

Experience has found that these products are not superior to NaCl solutions for identifying intrauterine pathologies, such as polyps and sub-mucosal fibroids. Some practitioners think their tendency to generate shadowing effects makes them less desirable than saline. For tubal assessment however, white contrast was found somewhat superior to negative ("black") media, such as saline. Even so, the value of these products for assessing tubal anatomy has been questioned because HSG (X-ray) remains so superior. We think that "white" products may prove to have a role for use in studying tubal functionality.

One specific embodiment of the present invention uses a phase-shifting uterine contrast medium (PSCM) to achieve the quality of uterine images obtained with hysterosonography while retaining the simplicity and great ease of use of regular vaginal ultrasounds. See, for example, Example 1 below. When instilled in the uterus with a regular embryo transfer catheter, the medium is thick and moderately distends the cavity. The particular PSCM used, which has the sonic characteristics of water, provides a negative or "black" contrast that allows excellent visualization of structures protruding in the cavity, such as endometrial polyps and/or sub-mucosal fibroids. Endowed with phase-shifting characteristics, the PSCM subsequently liquefies as its temperature rises and reaches body temperature. Once fluid, uterine distension ends and the PSCM is expelled.

Thus, one particular embodiment of the invention would be an aqueous gel for uterine ultrasound procedures, having "white" or "black" contrast enhancing properties. The gel is able to remain in the uterine cavity for the time of the ultrasound examination. After a set time, generally about 3-10 minutes, the gel liquefies and is expelled from the uterine cavity by uterine peristalsis. This expulsion is similar to the expulsion of the remaining quantities that did not already leak out of the uterus during prior art saline infusions, such as during hysterosonography.

In one embodiment, the time-limited viscosity is temperature dependent. Such a composition, for example, at room temperature or cooler would have a high initial viscosity when inserted into the uterus, until it reaches body temperature, at or by which point it loses viscosity, becomes more liquid, and is readily expelled. This permits the instillation of about 2-7 cc of the uterine gel in the endometrial cavity using a simple plastic catheter similar to those used for embryo transfer during an intrauterine insemination (IUI), using the cleaning procedure and precautions commonly applied for IUIs and all intrauterine procedures.

For an ultrasound procedure, the catheter and the speculum are then removed, and the ultrasound examination is performed as commonly done for all vaginal and abdominal ultrasounds. The uterine gel retains its viscous properties for sufficient time to complete the ultrasound examination, while benefiting from the same contrast enhancement obtained previously only with the complex "3-hand" hysterosonography procedure.

For hysteroscopy procedures, the same general type of medium typically could be used, but it generally would not need to provide contrast enhancement. Instead, such a medium usually would be optically transparent.

Hysteroscopy directly visualizes the inner aspect of the uterine cavity. The uterus needs to be artificially distended during the procedure in order to obtain panoramic visualization, rather than merely viewing the collapsed, folded walls of the uterus. Instruments used (hysteroscopes) combine optic fiber systems that provide illumination and allow viewing inside the uterine cavity, along with a mechanism for infusing a solution or gas at pressure sufficient to distend the cavity, and thereby permit vision of the uterine walls. Office hysteroscopy, limited to diagnosis only, uses miniaturized instruments in order to minimize the discomfort associated with their insertion through the cervical canal. However, miniaturization is limited by the complexity of current hysteroscopes, particularly the need to combine infusion devices with optic systems. These engineering limitations cause office hysteroscopy to remain fairly painful, thus hampering its regular and frequent use.

In an effort to miniaturize hysteroscopes and make the procedure less painful, contact hysteroscopy has been developed. Contact hysteroscopy consists of directly visualizing the endocervical and endometrial mucosa without distending the uterine cavity, and thus without obtaining a panoramic vision of the cavity. For this, rigid scopes are used featuring a single glass column, without a sheath encompassing an infusion device, to directly visualize the endocervical and endometrial mucosa. It permits some degree of histological diagnosis of the mucosa (endocervix or endometrium) when observed through a magnifying optical system. Hence, contact hysteroscopy serves to screen for cancer, histological causes of bleeding, and possibly for functional dating of the endometrium. Because the uterine cavity is not distended, however, contact hysteroscopy does not provide the panoramic vision necessary for diagnosing endometrial polyps or submucosal fibroids, the most common anatomical causes of dysfunctional uterine bleeding (DUB) that require surgical removal.

To free endoscopic exploration of the uterine cavity from the need to infuse a distending fluid or gas, an optically-transparent, phase-shifting medium (PSM) can be used. Such a novel medium may, for example, have the characteristics of being quite viscous at room temperature, providing distension of the uterine cavity for the duration of the endoscopic examination. It later liquefies upon reaching body temperature some minutes later, and is spontaneously expelled from the uterine cavity.

Such a temporary gel phase, or the viscous nature of other useful media, may be thermo-sensitive, as discussed above, or it may otherwise change after a period of time to a more liquid composition. Preferably, the medium has phase or viscosity shifting characteristics allowing it to change from a semi-solid or solid (such as a gel) to a more liquid form. The nature of this change—and the timing and trigger of the change—in physical characteristics of the medium may rely on one or more factors. For example, factors that may trigger the change in form can be due to various conditions, such as changes in pH, temperature, shear or pressure; presence of additional agents (for example, salts, solvents, acidic or basic substances); application of an electrical potential; or merely passage of time. The changed characteristics of the medium—once it becomes more fluid—allow it to be expelled like any other fluid upon completion of its phase-shifting process.

Depending on the medium's particular composition, such a medium can provide either a negative (black) or positive (white) contrast adjunct in ultrasound imaging. The phase-shifting or viscosity-shifting characteristics of the medium are preferable for use as an image enhancer for ultrasound imaging or endoscopic examinations of body or organ virtual cavities, such as the uterus.

The thermo-sensitive or other temporary viscosity of the invention may stem from specific gel-forming properties of certain ingredients useful in pharmaceutical compositions. For example, certain polymers, such as carbomer 934P, or carbomer 974P, may be useful in this manner to provide "temporary" viscosity. These polymers or other ingredients are known to be useful in providing a formulation that may be temporarily viscous, for example, in a composition that is viscous at a lower temperature, but that liquefies at or near body temperature, or a formulation that is viscous for a short period of time before liquefying. In addition, if desired, other agents or adjuvants also may be added to the composition, such as, for example, anti-infective agents, radio-opaque agents, agents to reduce graininess or otherwise to improve esthetics of the composition, or preservatives.

Of course, the present invention is applicable much more broadly, as would be readily recognized by anyone of skill in the art. For example, ultrasound or endoscopic examinations of other body cavities or organs (besides the vaginal or uterine cavity) would also be facilitated by the use of this invention. Similarly, other medical imaging procedures, such as x-ray or MRI, may also benefit from use of this invention.

In addition, while the temporary viscosity or solidity is a crucial aspect of most embodiments of the invention, the exact mechanism or means for liquefying or otherwise converting the composition is not itself important. The liquefaction or other phase or consistency conversion could result, for example, from a certain change in temperature, as contemplated above, or merely after passage of a certain amount of time, or upon addition of another agent, so long as the medium is initially viscous upon administration and then liquefies within a relatively short and predictable period of time or otherwise facilitates removal after a time sufficient to complete the procedure. Of course, the invention could also be practiced with a composition that is viscous enough to remain in place as desired, though it still is able to be expelled or removed without change in viscosity or consistency.

Particular advantages that the invention provides or supports for use with hysteroscopy include the following:

1. hysteroscopy without concomitant constant infusion of a solution or gas;
2. development of hysteroscope instruments of smaller diameter, without infusion devices (tubing, sheaths, etc), enabling the use of plastic or other material that may facilitate development of disposable instruments. These new simplified office hysteroscopes (disposable or not) could be connected to viewing cameras allowing instant viewing and recording of images or sequences of images.

The medium can be in a solid or semi-solid state prior to introduction into the body cavity, or can shift to a solid or semi-solid phase upon introduction into the body cavity. The medium could also be a semi-solid or solid before or after installation, but phase-shift upon introduction of another substance (eg. salts, acidic or basic substances, or solvents), which will cause a phase-shifting to occur and liquefy the medium.

Ingredients useful in the composition of the medium to provide the desired phase or viscosity properties include, but are not limited to, polymers (such as carbomers, methylcellulose, gelatin, agar, pectin, starches, high molecular weight polyethylene glycol), copolymers (such as poloxamers), and colloidal clays (such as bentonite or tragacanth). Thixotropic mixtures are also envisioned as potentially useful as the medium. Such mixtures of inorganic substances could be used as distending agents to enhance visualization.

Ideally, an image-enhancing product would be as non-toxic as possible for the uterine mucosa and gametes. Variants of the product should be developed to provide "negative" and "positive" contrast enhancing properties, respectively, for use in imaging procedures such as ultrasound procedures.

A negative contrast enhancer typically would be best for identifying uterine pathologies protruding in the uterine cavity such as sub-endometrial fibroids, endometrial polyps, and uterine synechiae and malformations, which are often likely to cause dysfunctional uterine bleeding or infertility. Positive contrast enhancer typically would be useful for imaging, for example, the Fallopian tubes. Use of negative and positive contrast enhancers progressively or otherwise in combination could serve for dual-contrast imaging as may be warranted under the particular circumstances.

The possible clinical applications of positive contrast products expands beyond the original use proposed for positive ultrasound contrast enhancers, such as Echovist. While Echovist has been used to visualize tubal anatomy, we envision that our positive ultrasound contrast enhancers will also serve for studying utero-tubal physiology, for example for studying sperm transport at mid-cycle by primarily retrograde contractility (i.e., away from the vagina—from cervix to fundus/tubes). Alternate use of the positive contrast enhancer would be, for example, for studying uterine contractility at the time of menses, when expulsion of uterine content by uterine peristalsis should normally be primarily antegrade (toward the cervix). Another variant of the uterine ultrasound contrast enhancer would be designed for studying vaginal-to-tubal transport in an attempt to assess the normal migration of sperm toward the uterus and the Fallopian tubes at mid cycle. Of course, additional uses may become obvious to one in the art.

Similarly, the ability to conduct office hysteroscopy without the need to continually infuse a solution or a gas opens new possibilities in that field, such as the development of instruments far smaller than existing ones. As pain and discomfort experienced during the procedure are the primary reasons limiting the number of examinations performed, the potential to use instruments of significantly decreased size is crucial. Currently, approximately half of the instrument size (diameter) is used to accommodate an infusion system, and the necessary coaxial sheaths dividing optic fibers from the infusion tubing.

If hysteroscopy procedures do not require a continuous infusion system (solution or gas), new innovative technical options for visualizing the uterine cavity may also be developed much more easily. Systems may be developed using only plastic optic fibers for the instruments, with the potential for inexpensive disposable intrauterine instruments or attachments, rather than the expensive non-disposables that need to be re-sterilized between patients. These smaller new instruments could approach the size of current plastic catheters used for intrauterine inseminations, allowing for relatively painless introduction into the uterine cavity after it is filled with the medium. Such advantages would allow the procedure to be used much more routinely, for example for diagnostic exploration to investigate common intrauterine pathologies, such as polyps or sub-endometrial fibroids or to evaluate infertile women for possible endometrial anomalies (polyp etc.).

Hence, an invention that allows hysteroscopies to be performed without requiring the constant or frequent infusion of a distending solution or gas has the potential to help revolutionize hysteroscopies by helping to make them truly painless, and therefore more routinely useful. Furthermore, it likely would allow development of new, markedly simpler and smaller, and possibly disposable, instruments, providing added convenience and benefits.

FIGS. 1 to 6 illustrate the results attained with use of the instant invention, in ultrasound and endoscopy procedures. FIGS. 1A, 2A, 3A, and 4A are images from plain ultrasounds (without contrast medium), conducted on four different patients. FIGS. 1B, 2B, 3B, and 4B are images of the very same patients, obtained from hysterosonographies using the instant invention. In each instance, use of the instant invention revealed a polyp or fibroid that was not observed with plain ultrasound, but without the difficulties and inconveniences of classical hysterosonographies.

And FIGS. 5 and 6 are images obtained in two patients during hysteroscopies using the instant invention. These procedures disclosed significant physiological abnormalities with the clarity of classical hysteroscopy but without the difficulties, discomfort and inconvenience normally attributed to hysteroscopy procedures.

EXAMPLES

A sample formulation may be prepared as follows. 3 g carbomer 934P is sifted into 900 ml of purified water at room temperature while agitation is applied to the water. Once all the carbomer is mixed into the water, 10 g sorbitol may be added to reduce graininess. Appropriate amounts of purified water (to produce a total volume of 1000 ml) and sodium chloride (to make the resulting product isotonic and isosmolar) are added to the mixture. The mucilage that is formed is then mixed rapidly using low shear for 15-30 minutes. Allow the mixture to stand for 30 minutes without stirring to allow any foam to break. Adjust pH with sodium hydroxide to 7.4. Deaerate the mixture.

Examples 1 and 2 below reflect studies in which we used a similar composition that is commercially available. Lacryvisc™ is an ophthalmic gel manufactured by Alcon, containing 0.3% carbomer 934P, sorbitol, sodium hydroxide (pH buffer), benzalkonium chloride (preservative) and purified water. The Lacryvisc was cooled to about 35-40 degrees F. before it was instilled into the uterus for these procedures. Generally, however, we would prefer to use a formulation that (1) does not require cooling before use, and (2) is terminally sterilized and thus does not need a preservative.

Example 1

Contrast Ultrasound —53 Patients

Design—Prospective pilot feasibility study in infertile women and women with dysfunctional uterine bleeding (DUB).

Materials and Methods —53 women consulting for infertility (n=27) or DUB (n=26) were studied. After a conventional vaginal ultrasound was performed, all underwent contrast ultrasound examination. For this, 3-7 cc of a negative (black) phase shifting uterine contrast medium ("PSCM") was infused in the uterine cavity using a 3.5 Frydman embryo transfer catheter. The uterine catheter was then removed and another vaginal ultrasound was performed.

Results—In all women, the uterine cavity remained distended for ≧3 minutes, leaving a ≧3.5 mm thick "black" interface in the uterine cavity. In all patients uterine distension and medium had disappeared after 10 minutes. In 21 of 26 women presenting with DUB, contrast ultrasound revealed an intrauterine pathology that was subsequently confirmed by hysteroscopy and histology. In 14 of them, conventional vaginal ultrasound had not provided a definitive diagnosis.

Discussion—The examination using the inventive gel was not painful. Patients did not complain of discomfort and did not require pain medication.

Conclusion—This reports the development of a novel PSCM, which generates a time-limited moderate distension of uterine cavity, providing a sono-transparent ("black") inter-phase. This offers "contrast ultrasound" vision, which greatly facilitates the positive diagnosis of intrauterine structures such as polyps and fibroids. Contrast ultrasound of the uterus using PSCM may revolutionize uterine echography, as it provides images of hysterosonography quality, while retaining ease of use and the simplicity of general trans-vaginal ultrasounds.

Example 2

Endoscopic Vision of the Uterine Cavity —7 Patients

Design—Pilot feasibility study in women scheduled for surgical hysteroscopy, using optically-transparent phase shifting medium ("PSM").

Materials and Methods—The PSM was tested in 7 women immediately before a scheduled surgical hysteroscopy. 7-10 cc of PSM was infused in the uterine cavity using a common embryo transfer catheter after patients underwent cervical dilatation. After the embryo transfer catheter was removed, the conventional hysteroscope was introduced and endoscopic exploration undertaken without connecting the infusion system. After direct visualization was completed, conventional hysteroscopy was conducted using an infusion of a distending solution.

Results—The uterine cavity, slightly distended by the viscous nature of the PSM at the time of insertion, was easily explored with panoramic endoscopy. The viscous nature of the PSM also prevented it from mixing with blood originating from the uterine mucosa, which would have blurred vision. Polyps and protruding sub-mucosal fibroids were identified in 1 and 3 cases, respectively. In one case, an unsuspected uterine synechia was identified. In the remaining 2 cases, no patent pathologies were seen. Progressively, as temperature of the PSM rose and reached normal body temperature (after >3 min), viscosity and distension of the uterine cavity were lost, thus terminating the possibility for further endoscopic vision of the cavity. In all cases, the subsequent conventional hysteroscopy confirmed the endoscopy findings.

Discussion—Vision of the entire uterine cavity was good, allowing thorough exploration and positive identification of the pathology present in all cases. Photographs were taken in all cases to document findings. Confirmation was obtained in all cases by a subsequent operative hysteroscopy performed immediately after. To the best of our knowledge, this represents the first instance of performing a panoramic (rather than contact) hysteroscopy without concomitantly infusing or distending solution or gas.

Conclusion—These results confirm the feasibility of using a PSM for obtaining endoscopic vision of the uterine cavity without requiring a concomitant infusion of a distending fluid or gas. This innovation carries the potential of revolutionizing office endoscopy of the uterus.

A prototype medium will be tested in office hysteroscopies conducted without cervical dilatation (which will minimize undesired expulsion of the medium) and anesthesia.

Example 3

Positive and Negative Contrast Uterine Gels

A negative contrast gel would be particularly appropriate for use to enhance the contrast of uterine ultrasounds. Such a negative medium would facilitate the diagnosis of uterine pathologies such as sub-mucosal fibroids, endometrial polyps, endometrial synechiae (scars), uterine malformations and all uterine pathologies having endometrial repercussion and/or ultrasound expression. Potentially, the negative gel can permit imaging part or all of one or both Fallopian tubes.

Uterine exposure to progesterone or progestins, such as with oral contraception, is likely to prolong the presence of the gel because of the utero-relaxing properties of progesterone and progestins. And other possible applications will be sought for enhancing negative contrast of other forms of imaging of the uterus and tubes, including for example by MRI and CT scans.

Positive contrast media will also be useful. A positive contrast formulation likely will gain its positive ultrasound contrast characteristics from calibrated gas bubbles or sono-refractive particles such as micro-spheres, macro-polysaccharides/starches, etc.

As is the case with other positive ultrasound contrast products such as Echovist, a positive contrast thermo-sensitive gel accordingly to the instant invention will be particularly useful for visualization of the proximal portion of the Fallopian tubes. Yet, contrary to existing products, our positive contrast uterine contrast gel will also enable easier assessment of the physiology and patho-physiology of contractility of the utero-tubal unit. The positive gel, deposited in the uterine cavity using, for example, an embryo transfer catheter, could be monitored for actual displacement toward the Fallopian tubes by assessing the tubal passage of air particles or other substances retained for conferring the gel's echogenicity. Various tests readily could be conducted to determine the optimal size of air bubbles or micro particles for the purpose of assessing sperm transport.

Other possible applications for positive contrast gels will be apparent, including in various forms of association with negative contrast gels, such as for improving visualization of retrograde transport of uterine content. Possible applications of ultrasound imaging with positive enhanced contrast include examining and treating conditions linked to certain forms of uterine dyskinesia, such as endometriosis or dysmenorrhea, and various forms of yet unexplained fertility issues.

The diagnostic uterine gel (positive or negative contrast) will be designed to be free of embryotoxicity. After verifying pH, osmolality and other pertinent physical characteristics, the medium will be tested for embryo toxicity in the 2-cell mouse embryo system and, if deemed necessary, in a human embryo system (such as available in Sweden). The lack of embryo toxicity will permit the practitioner to use the uterine gel for functional testing of utero-tubal functionality, such as for testing the functionality of uterine contractility. This includes testing for retrograde contractility at the time of ovulation, utero quiescence during the luteal phase, and expulsive antegrade contractions normally prevalent during the early follicular phase (menses). If the gel cannot be made completely safe for pregnant women, it would be tested to confirm safe use in non-pregnant women without adversely affecting fertility. We expect that such a gel could easily be formulated for safe use either way.

Example 4

Primary Indications for Use of the Invention for Uterine Ultrasound Examination

The physical characteristics of the medium (solid, semi-solid or gel-like) allow the creating of a relative distension of the uterine cavity, which is normally only a 'virtual' cavity, thereby improving imaging of its surface. The characteristics of the medium are essential to how it is used practically. The solid/semi-solid characteristics allow maintaining a relative distension of the uterine cavity for a time sufficient to allow completion of the ultrasound examination. The subsequent liquefaction or other release of the medium allows its spontaneous expulsion from the uterus like any other fluid, such as menstrual blood.

The echographic characteristics of the medium (either, decreased echogenicity or "negative contrast" or enhanced echogenicity or "positive contrast") enhance contrast with the surrounding structures (endometrium and myometrium) depicted on ultrasounds in various shades of gray.

Enhancement of image quality of the uterus and uterine tubes is thus obtained from:
1. Distension of the uterine cavity while allowing sufficient retention of the contrast medium for the duration of the examination.
2. Enhancing the contrast, using a negative contrast medium (black) or positive contrast medium (white) in the uterine cavity.

The invention would be particularly appropriate for use in examining the uterus, for example, in the following situations:
1. Identifying anatomical pathologies present in the uterine cavity such as uterine polyps and/or sub-mucosal fibroids.
2. Identifying anatomical pathologies of the uterine tubes and determining their patency (particularly with "positive" uterine phase-shifting contrast medium).
3. Identifying functional pathologies of the uterus and tubes associated with abnormal pattern of contractility and displacement of uterine content, including
   a) anomalies of retrograde contractility in the late follicular phase associated with defective sperm transport and infertility/sub-fertility; and
   b) anomalies of contractility at the time of menses when uterine contractility plays a pivotal role in the forward emptying of uterine content (menstrual blood), possibly resulting in, or associated with, retrograde bleeding and endometriosis.
4. Performing diagnostic hysteroscopies without requiring continuous or sporadic infusion of a fluid or gaseous solution for distending the uterine cavity, allowing true non-contact hysteroscopy without instillation of gas or fluid.
5. Conducting forms of uterine imaging other than ultrasound, for example with hystero-salpingograms (HSG), CT (Computed Tomography) scans, and MRI procedures. For HSG, a mixture of the phase-shifting contrast medium with a X-ray contrast solution (iodine based or other) would permit the practitioner to avoid needing to insufflate the solution, instead allowing deposit of the solution directly in the uterine cavity.

Example 5

Use of the Invention with Organs Other than the Uterus

The invention would be appropriate for use in examining organs other than the uterus, for example, in the following situations:
1. As contrast enhancer (positive or negative) for imaging of organs other than the uterus and the Fallopian tubes, providing persistence of the contrast enhancing properties for the duration of the examination.
2. To provide temporary distension for imaging of normal body cavities, such as sinuses, or abnormal ones, such as fistulas and or other collections.
3. As contrast enhancer for investigating other body cavities with ultrasound and other forms of medical imaging, such as CT scans, MRIs, and X-rays.
4. To allow endoscopic evaluation inside normal or abnormal body cavities, such as fistulas.

Example 6

Other Possible Uses of the Inventive Medium

The invention could also be used in combinations with other forms of contrast medium. For example, the medium can be combined with iodine and other forms of X-ray contrast agents. Such a combination would provide prolonged presence in body or organ cavities, such as the uterine cavity and Fallopian tubes, and distension of such cavities without need to maintain a source of external pressure and ongoing infusion of gas or liquid.

Any and all publications and patent applications mentioned in this specification are indicative of the level of skill of those skilled in the art to which this invention pertains. All publications and patent applications mentioned herein are hereby incorporated by reference to the same extent as if each individual publication or application was specifically and individually incorporated by reference.

It is to be understood that the invention is not to be limited to the exact configuration as illustrated and described herein. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A method of conducting a medical imaging procedure on a body or organ cavity comprising:
preparing an image enhancing, viscosity-shifting composition for use in a medical imaging procedure, wherein the composition maintains an initial viscosity or consistency for a time sufficient to conduct the imaging procedure, upon or after introduction to a body or organ cavity, to remain substantially in place within the cavity, and the composition subsequently reduces in viscosity or consistency over a relatively short period of time, sufficiently so as to allow the composition to be easily expelled or removed from the cavity within about 7 to 20 minutes after the imaging procedure is completed;
placing the image enhancing, viscosity-shifting composition into the body or organ cavity;

conducting the imaging procedure while the composition maintains its initial viscosity;

allowing the composition to then, after the procedure is completed, reduce in viscosity or consistency over the relatively short period of time; and then removing or allowing expulsion of the reduced viscosity or reduced consistency composition from the cavity after conducting the imaging procedure.

2. The method of claim 1, wherein the composition is formulated to be suitable for use in vaginal ultrasound examinations.

3. The method of claim 2, wherein the composition provides negative contrast enhancement.

4. The method of claim 1, wherein the composition liquefies or decreases in viscosity in response to a particular change in temperature of the composition.

5. The method of claim 4, wherein the composition provides positive contrast enhancement.

6. The method of claim 1, wherein the composition comprises a polymer that provides an initial viscosity upon delivery for a certain period of time and later provides a different viscosity in response to a change in temperature.

7. The method of claim 6, wherein the viscosity of the polymer is reduced as the temperature increases.

8. The method of claim 1, wherein the composition further comprises one or more adjuvants or treating agents.

9. The method of claim 8, wherein the adjuvants or treating agents include an anti-infective agent or a radio opaque agent.

10. The method of claim 1, wherein the composition maintains its initial viscosity or consistency for about 3 to 10 minutes, after which the viscosity or consistency rapidly decreases so as to allow the composition to be easily expelled or removed from the cavity after the imaging procedure is completed.

11. The method of claim 1, wherein the composition remains substantially in place within the cavity for a period of time sufficient for the imaging procedure to be completed without need for replenishment during the procedure.

12. The method of claim 1, wherein:

the organ cavity is the uterine cavity or Fallopian tubes;

the composition liquefies or decreases in viscosity in response to a particular change in temperature of the composition; and the expulsion or removal of the composition from the uterine cavity or Fallopian tubes is substantially complete within about 20 minutes.

13. A method of conducting a medical imaging procedure on a body or organ cavity comprising:

preparing an image enhancing, viscosity-shifting composition for use in a medical imaging procedure into the cavity, wherein the composition (a) is initially a solid, semi-solid, or gel upon or after introduction to a body or organ cavity and for a time period sufficient to conduct the imaging procedure, so that the composition does not need to be continually or frequently administered or replenished during the imaging procedure, and (b) then liquefies or decreases in viscosity over a relatively short period of time, so that it can be easily expelled or removed from the cavity, placing the image enhancing, viscosity-shifting composition into the body or organ cavity;

conducting the imaging procedure while the composition maintains its initial viscosity;

allowing the composition to then, after the procedure is completed, reduce in viscosity or consistency over the relatively short period of time; and removing or allowing expulsion of the liquefied or reduced viscosity composition from the cavity after conducting the imaging procedure.

14. The method of claim 13, wherein the composition is formulated to be suitable for use in vaginal ultrasound examinations.

15. The method of claim 14, wherein the composition provides negative contrast enhancement.

16. The method of claim 13, wherein the composition liquefies or decreases in viscosity in response to a particular change in temperature.

17. The method of claim 16, wherein the composition provides positive contrast enhancement.

18. The method of claim 13, wherein the composition rapidly liquefies or decreases in viscosity after about 3 to 10 minutes so as to allow the composition to be easily expelled or removed from the cavity after the imaging procedure is completed.

19. The method of claim 18, wherein the expulsion or removal of the composition from the cavity is substantially complete within about 7 to 20 minutes.

20. A method of conducting a medical imaging procedure on a body or organ cavity comprising:

preparing an image enhancing, viscosity-shifting composition for use in a medical imaging procedure into the cavity, wherein the composition (a) has and maintains sufficient viscosity so that it does not need to be continually or frequently administered during the imaging procedure, and (b) then liquefies or decreases in viscosity over a relatively short period of time so that it can be easily expelled or removed from the cavity after sufficient time for the imaging procedure to be completed, placing the image enhancing, viscosity-shifting composition into the body or organ cavity;

conducting the imaging procedure while the composition maintains sufficient viscosity, before it rapidly liquefies or reduces in viscosity after completion of the imaging procedure; and then removing or allowing expulsion of the liquefied or reduced viscosity composition from the cavity.

21. The method of claim 20, wherein the composition rapidly liquefies or decreases in viscosity after about 3 to 10 minutes so as to allow the composition to be easily expelled or removed from the cavity after the imaging procedure is completed.

* * * * *